(12) United States Patent
Rey

(10) Patent No.: US 6,497,648 B1
(45) Date of Patent: Dec. 24, 2002

(54) DEVICE FOR APPLYING ELECTROMAGNETIC THERAPY

(76) Inventor: Omar Vicente Rey, Jacinto Rosso-127, Temperley - Provincia de Buenos Aires (AR)

(*) Notice: Subject to any disclaimer, the term of this patent is extended or adjusted under 35 U.S.C. 154(b) by 0 days.

(21) Appl. No.: 09/618,668

(22) Filed: Jul. 18, 2000

(51) Int. Cl.$^7$ .................................................. A61N 1/00
(52) U.S. Cl. ............................................................ 600/14
(58) Field of Search .................................. 600/9, 10, 11, 600/12, 13, 14, 15

(56) References Cited

U.S. PATENT DOCUMENTS

| | | | |
|---|---|---|---|
| 4,454,883 A | * 6/1984 | Fellus | 607/3 |
| 4,993,413 A | * 2/1991 | McLeod et al. | 607/2 |
| 5,267,938 A | * 12/1993 | Konotchick | 600/9 |
| 5,437,600 A | * 8/1995 | Liboff et al. | 600/9 |
| 6,099,459 A | * 8/2000 | Jacobson | 600/13 |

* cited by examiner

*Primary Examiner*—Kevin Shaver
*Assistant Examiner*—Pamela Wingood
(74) *Attorney, Agent, or Firm*—Greer, Burns & Crain, Ltd

(57) ABSTRACT

A device for applying electromagnetic therapy by sequentially generating pulsing electromagnetic fields for treating a patient in need of the therapy, the device comprising a high frequency signal generator, a low frequency signal generator, a comparator and an amplifier for treating the signals generated by the generators for generating pulsing fields that can be applied to a desired part of the body of a patient through a radiating coil, the device also including a monitoring circuit for monitoring the application of the electromagnetic pulsating field.

12 Claims, 3 Drawing Sheets

DEVICE FOR APPLYING ELECTROMAGNETIC THERAPY

BACKGROUND OF THE INVENTION

1. Field of the Invention

The present invention relates to the medical field of the electromagnetism applied to the therapy of some diseases like osteoporosis, bone and tissue diseases and the like. More particularly, the invention relates to a device for sequentially generating pulsing electromagnetic fields intended for therapeutic use in bone and muscle diseases. The invention also relates to an apparatus, preferably a bed, for applying electromagnetic fields to a patient in need of electromagnetic therapy.

2. Description of the Prior Art

It is well known to provide magnetic therapy by subjecting a patient to a magnetic field from permanent magnets and several magnetic devices applied in different therapies, mainly in kinesiology.

These devices are mainly based on at least two coils that generate a stationary magnetic field. The diseased parts of the patient have to be passed through the magnetic field lines.

The field strength that is necessary for these treatments requires the use of relatively large coils, therefore, these devices are bulky and quite heavy.

It would be therefore convenient to have a new device for applying electromagnetic therapies and capable of being portable and operable with batteries and also capable of being combined with an apparatus, like a therapeutic bed, for treating larger areas of the body of a patient resting on the bed.

SUMMARY OF THE INVENTION

It is therefore one object of the present invention to provide a circuit or device overcoming the above problems and drawbacks, the device being capable of sequentially generating pulsing electromagnetic fields and comprising at least two signal generators, one signal being a high frequency signal and another signal being a low frequency signal, a comparator and an amplifier for treating the signals for generating pulsing fields that can be applied to a desired part of the body of a patient through irradiating or radiating means, the device also including a monitoring circuit for monitoring the application of the electromagnetic pulsating field.

It is still another object of the present invention to provide a device for applying electromagnetic therapy by sequentially generating pulsing electromagnetic fields for treatment of bone diseases and osteoporosis, the apparatus being of the type generating low power electromagnetic pulses, the device comprising a high frequency signal generator; a low frequency signal generator comprising an astable multivibrator including a controlling means comprising a selector connected to a plurality of capacitive reactances that may be selectively and alternatively enabled for varying the charging time between 1.25 and 1.5 microseconds; a comparator having inputs connected to respective outputs of said signal generators; an amplifier circuit having an input connected to an output of the comparator, for amplifying an output signal of the comparator comprised of a high frequency pulse train; a converter circuit connected to an output of the amplifier circuit, for monitoring the amplifier circuit output; and an inductive reactance connected to the output of the amplifier circuit and comprising a means for radiating the pulsing electromagnetic fields, said radiating means being defined by an open circuit coil, wherein one terminal of the coil is connected to the output of said amplifier circuit by means of a coaxial cable.

It is a further object of the present invention to provide a therapeutic apparatus for applying pulsing electromagnetic fields for treating a patient in need of the therapy, the apparatus comprising the above described device and a resting table for receiving the patient, the radiating means comprising at least one radiating strap movably arranged along the table, the strap being selectively located in a proper position for irradiating a desired part of the body of the patient.

It is even another object of the present invention to provide an electromagnetic pulse generator that, unlike the traditional devices using stationary magnetic fields, provides pulsing fields that are extremely effective for treating different bone diseases, and particularly in the case of osteoporosis, with the recovery periods of time which are significantly shorter.

It is still another object of the invention to provide a device with better therapeutic effectiveness by using pulsing fields based on the generation of a train of high frequency waves, preferably 60 microsecond pulses in sequences varying between 1.25 and 1.5 seconds in relation to the position selected, with a controlling means comprising a selector for selecting different capacitive reactances.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
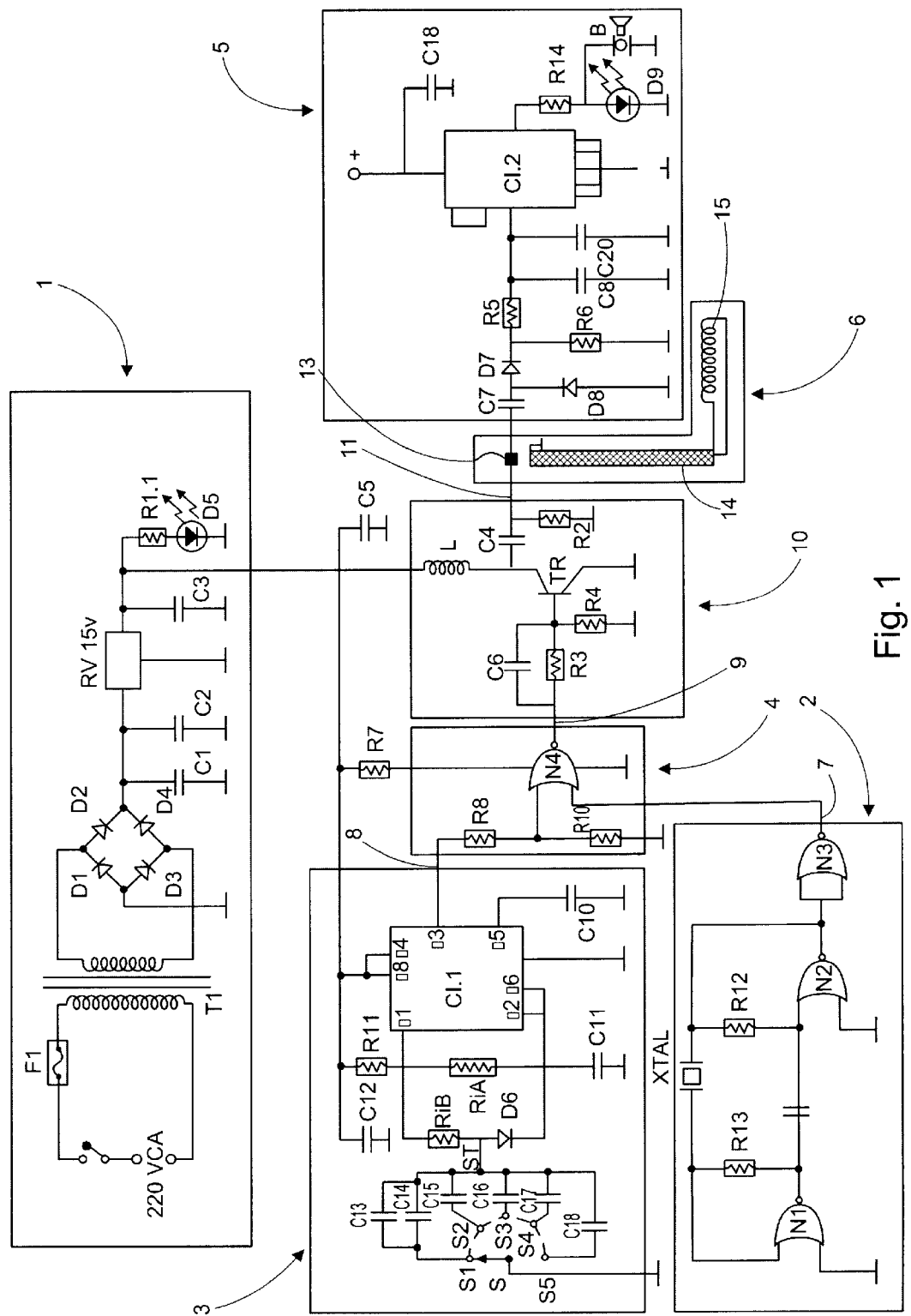
FIG. 1 shows a schematic diagram of the circuit or device according to a preferred embodiment of the invention.

Now referring in detail to the drawings it may be seen from FIG. 1 a device for the sequential generation of pulsing electromagnetic fields intended for therapeutical use based on two signal generators and a means for radiating said fields. This device is basically a circuit comprising a regulated supply source 1 for feeding the circuit, a high frequency generator 2 for generating high frequency signals and a low frequency generator 3 for generating low frequency signals, generator 3 including controlling means S. Generators 2, 3 include respective outputs 7, 8 connected to corresponding inputs of a comparator 4, the comparator having an output 9 connected, in the one hand, to a converter circuit 5 for monitoring the comparator output and, on the other hand, to radiating means 6 for irradiating pulsing electromagnetic fields.

More particularly, regulated supply source 1 comprises a 220V/18V transformer T1, with a rectifier bridge having diodes D1, D2, D3, D4, filtering capacitors C1, C2 and 15V voltage regulation RV. Source 1 is also provided with a LED D5 connected to a resistor R1.1, the resistor operating as a pilot light to indicate a turn on condition.

High frequency signal generator 2 comprises one 8,867238 MHz crystal oscillator. This circuit comprises three NOR gates N1, N2 and N3 having two inputs. The output of the first gate N1 is connected to the input of the second gate N2 through a tuned coupler C19. The output of the second gate N2 is connected, on the one hand, to the two inputs of the third gate N3 in inverting configuration and, on the other hand, to a feedback loop R12-Xtal-R13. Finally, the output of the third gate N3 is connected to output 7 of generator 2.

Generator 3, for generating low frequency signals, comprises an astable multivibrator with a linear integrated circuit CI.1, preferably an IC 555. Integrated circuit CI1 has two terminals 14 and 18 connected the positive supply pole and terminal I1 at the negative supply pole.

Low frequency signal generator 3 also has controlling means S consisting of a control selector having a predetermined range, the selector having terminals S1, S2, S3, S4 and S5 connected to respective capacitors C13, C14, C15, C16, C17 and C18 that can be selectively and alternatively activated or enabled. These capacitors have a common connection ST, at the output in the middle of controller S, in a such a way that the activated or selected capacitor together with resistors R11, Ria, Rib and capacitor C11, comprise a stage for determining the charging period of time. Diode D6 together with capacitor C11 and resistor Ria comprise a step or stage for determining the discharging time period.

Terminal I3 of integrated circuit CI.1 is the output of astable multivibrator that is connected with the inlet of comparator 4. Comparator 4 comprises a NOR gate N4 with two inputs, with one of these inputs connected to the output of astable multivibrator 3 by means of attenuating resistors R8 and R10, and the other input of gate N4 connected to output 7 of 8,867238 Mhz crystal oscillator 2. The output of gate N4 is the output of comparator 4 and is connected to an amplifier 10. A feedback resistor R7 is connected to gate N4 and to a capacitor C5 and capacitor C12, both feedback uncoupling capacitors.

Amplifier 10 has an input defining a coupling stage connected to the output of comparator 4, comprising a resistor R3 connected in parallel to a capacitor C6. These components, together with a biasing resistance R4, are connected to the base of a transistor TR with a cut off frequency not lower than 15 MHz, the emitter of the transistor being connected to ground. The collector of the transistor is, on one side, biased by a coil L and, on the other side, is connected to a capacitor C4 and a coupling resistor R2 which is connected to ground, thus defining the output of amplifier 10.

Output 11 of amplifier 10 is connected to converter 5 for monitoring the output signal of the invented device or circuit. This converter 5 comprises a signal integrating stage comprising two diodes D7 and D8 to the anode and cathode of which, input capacitor C7 is respectively connected. The anode of diode D8 is connected to ground, and the cathode of diode D7 is connected to resistors R6 and R5. Resistor R6 has one terminal thereof connected to ground and resistor R5 is connected to the input of integrated circuit CI.2 in a common connection with respective terminals of two capacitors C8 and C20, the opposite terminals of capacitors C8 and C20 being connected to ground.

The output terminal of integrated circuit CI.2 is connected, through a limiting resistor R14, to a LED D9 and a buzzer B. A capacitor C18 is connected to the power-connected inlet of CI.2 for filtering pulses appearing at such inlet.

Irradiating or radiating means 6, for radiating or emitting pulsing electromagnetic fields, is arranged at the output of amplifier 10. The radiating means consists of a coil 15 formed by a flat cable, preferably comprising 34 conductors, connected to a printed circuit board, forming an assembly comprising an antenna tuned to 8,867238 MHz and connected to amplifier 10 by means of a 75 ohm coaxial cable 14 terminating in a BNC plug 13.

Figure 2:
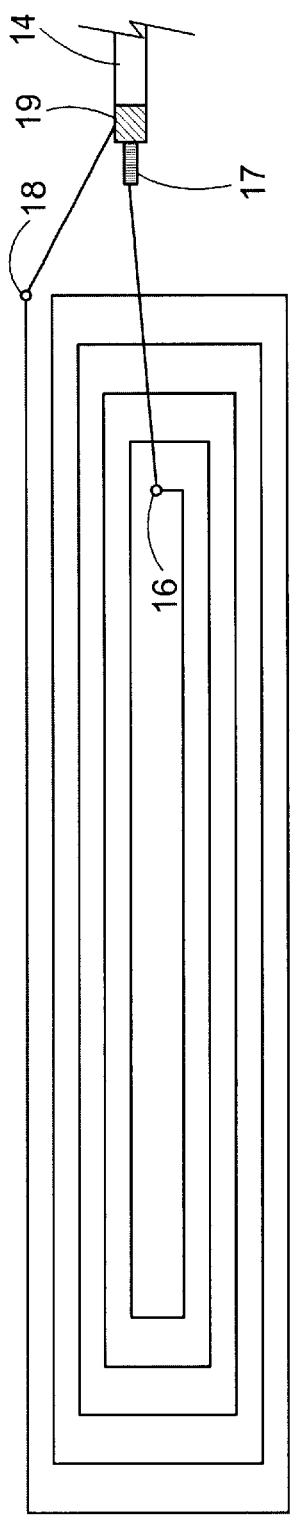
FIG. 2 diagramatically shows a first embodiment of a closed circuit coil that defines a first type of electrode that is applicable to the device of the present invention.

As shown in FIG. 2, radiating means 6, according to an alternative embodiment of the invention, may comprise a coil 20 may have a first terminal 16 connected to the core or "live" conductor 17 of coaxial cable 14 and a second terminal 18 is connected to the shielding 19 cable 14, in order to form the connection to ground of coil 15, thus defining a closed circuit electrode. Very good results have been achieved in this case with frequencies of 40 Hz and down.

Figure 3:
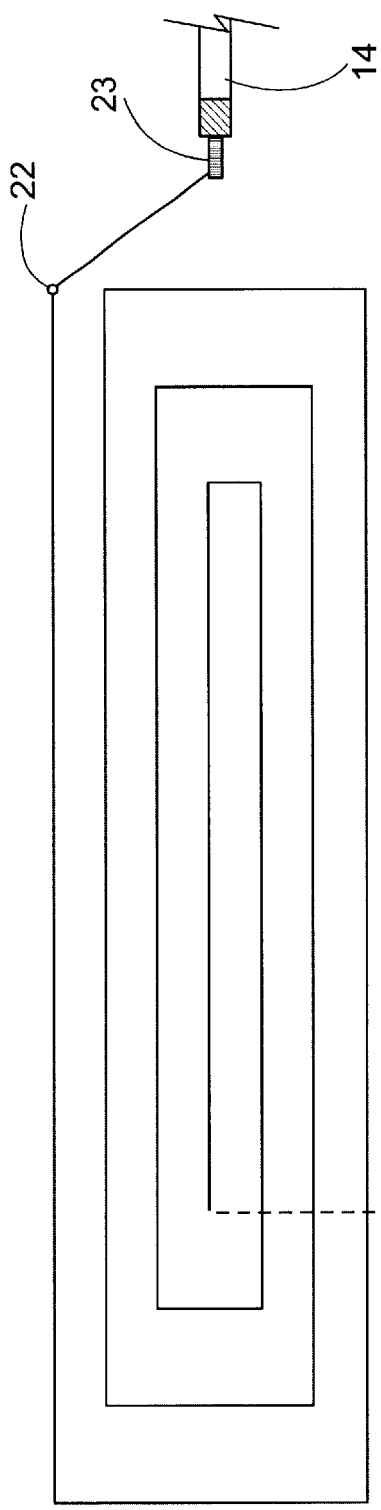
FIG. 3 diagramatically shows a preferred embodiment of an open circuit coil that defines a second type of electrode that is applicable to the device of the present invention.

According to another embodiment of the invention, shown in FIG. 3, radiating means 6 may comprise a coil 21 having a first terminal 22 connected to the core conductor 23 of coaxial cable 14, and a second terminal 24 remaining free of any connection, thus defining an open circuit electrode. Excellent results have been achieved with this embodiment, for instance acting on pain and inflammations in the diseased area, with frequencies of 40 Hz and up.

Coils 20 and 21 of FIGS. 2 and 3 respectively are for external use, and are formed on a printed circuit, but preferably are defined with flat cables. Taking into account the flexibility of this type of cable, the radiating means, or electrode, can be placed onto the diseased part of the body of the patient under treatment, or, otherwise, such diseased body's part may be surrounded or wrapped with the electrode. Coils 20 and 21 can be construed with flat cables having preferably 34, 50 or 64 conductors.

Figure 4:
FIG. 4 diagramatically shows another embodiment of an open or closed circuit coil that defines another electrode that is applicable with the device of the present invention.

The embodiment shown in FIG. 4 forms an elongated microelectrode, where a coil 25 is wound on a plastic core for applying in small holes or cavities of the patient body, achieving, for instance an optimum healing of the pathologies under study.

The above described electrodes are connected by means of a 75 ohm coaxial cable 14 to the output of the device amplifier with a 90° rotary BNC type connector, such as connector 13 that provides durability and reliability.

During the operation of the inventive circuit, the assembly comprising the feedback loop R12-Xtal-R13 and coupling capacitor C19, in crystal oscillator 2, allow the circuit to oscillate at a 8,867238 MHz frequency determined by the crystal Xtal, thus generating a square wave of that frequency.

The actuation of the controlling means S in the astable multivibrator 3 allows to vary the capacitive reactance at the selector output and therefore to vary the charging time period that, according to predetermined values, varies between 1.25 and 1.5 microseconds. At the same period of time, during the fixed discharging time of 60 microseconds, diode D6 blocks the selectively enabled capacitor. As a result, there is a square wave oscillation at the output of this circuit, where the "1" logic state lasts between 1.25 and 1.5 microseconds and the "0" logic state lasts 60 microseconds.

The two above described signals, that are generated by the respective signal generators 2 and 3 reach the inputs of NOR gate N4 of comparator 4. This gate shall supply "1" logic value at the output thereof when both inputs of the gate are "0" logic value. Therefore, there will be value "1" at the output with each passing through value "0" of the 8,867238 MHz oscillator signal, provided it occurs during the 60 microseconds when astable oscillator 3 is in value "0".

The output signal of comparator 4 shall thus form a train of high frequency pulses of 60 microseconds duration and in sequences varying between 1.25 and 1.5 microseconds in relation to the value of the capacitor selectively enabled by the controlling means S.

The oscillations sequences of 8,867238 MHz amplified with 1W power is obtained at the output of transistor TR of amplifier 10.

The integrated circuit CI.2 of the monitoring converter 5 operates to adapt or adjust the signal to the requirements of LED D9 and buzzer B. Thus, LED D9 provides for a visual monitoring and buzzer B provides an audio monitoring, with the frequency of which varying in agreement to the variations of the electromagnetic field generated by the circuit.

Finally, radiating means 6, depending on the embodiment illustrated in FIGS. 2–4 will permit the application of the generated electromagnetic fields in desired localized areas of the body.

It is quite clear to any skilled in the art that the inventive device requires less power consumption as compared to conventional magnetic devices, the device of the present invention requires a smaller source of power supply. The difference is such that this device can operate with two 9V batteries, whereby a connection to higher voltages, such as 220V, is unnecessary. Therefore, while on the one hand, the safety for the patient and the operator is remarkably increased, on the other hand, the factor of fear to the electrical power, that usually discourages many patients, is removed.

The present invention also solves the above noted drawback relative to the high weight and volume of the equipment, since due to its own structure and principle of operation, the device is of less size and weight and is quite portable. Due to its structure and autonomous operation, by operating with small batteries, the barrier that up to the present prevented a wider application of these therapies in rural areas is broken. Likewise, the therapist may continue with the treatment even in cases of interruption of the electrical power supply or sharp drops in the service voltage.

Taking into account all the above advantages the invention is extremely suitable for different therapies, including kinesiology therapies, and is particularly suitable for all therapies related to the treatment of bones.

Therefore, an invention is provided that shall be received with satisfaction by all the community, since it contributes to improve the quality of life.

Figure 5:
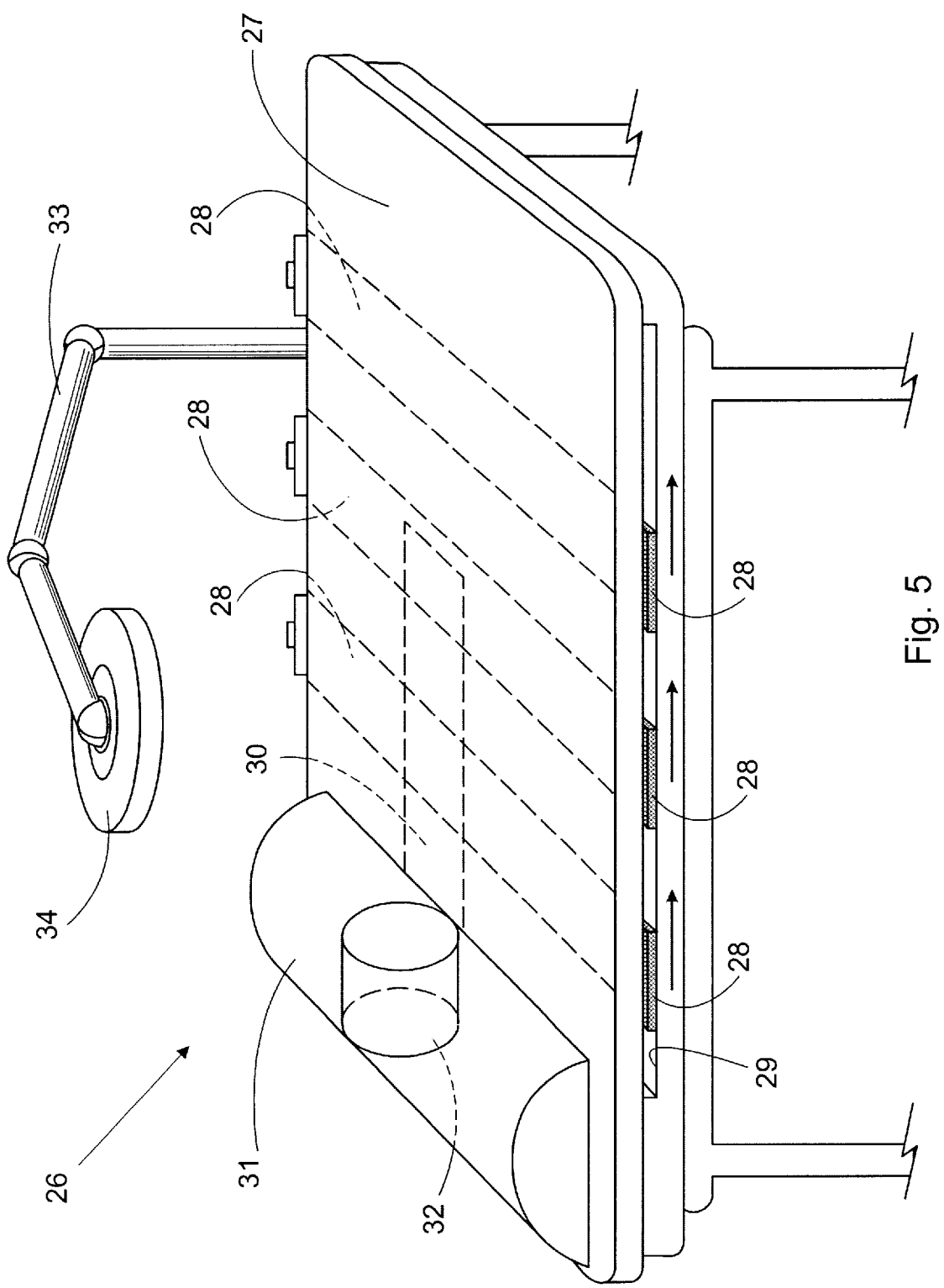
FIG. 5 is a perspective diagramatic view of an apparatus comprising a therapeutic table including the circuit or device of the invention.

According to a particular application of the circuit or device of the invention, schematically shown in FIG. 5, a therapeutic apparatus, generally indicated by reference number 26, for applying pulsing electromagnetic fields for treating a patient in need of the therapy. Therapeutic apparatus 26 preferably comprises a stretcher, bed or resting table 27 for receiving the patient, and the circuit or device of FIGS. 1–4 for applying a pulsing electromagnetic field to localized areas of the body of the patient that rests onto the table. Radiating means 6 comprises at least one radiating strap or band 28 comprising one or more electrodes like the ones of FIGS. 2, 3. The straps are arranged under table and, preferably, in a channel 29 wherein the straps are transversely located and slidably received to move the straps along the longitudinal dimension of the table in order that the straps may be selectively located in the desired and proper position according to the area to be irradiated in the body of the patient. The table also includes a fixed longitudinal strap 30 in a position to be aligned with the spine of the patient.

At one end of the table a pillow 31 is provided for bearing the head of the patient, the pillow also having radiating means 6 comprising, in this embodiment, a cylinder 32 also for irradiating the head and/or neck of the patient. A movable arm 33 is also provided including another electrode or irradiator 34 capable of being located onto a desired part of the body of the patient.

While preferred embodiments of the present invention have been illustrated and described, it will be obvious to those skilled in the art that various changes and modifications may be made therein without departing from the scope of the invention as defined in the appended claims.

I claim:

1. A device for applying electromagnetic therapy by sequentially generating pulsing electromagnetic fields for treating a patient in need of the therapy, the apparatus being of the type generating low power electromagnetic pulses, the device comprising:

a high frequency signal generator, a low frequency signal generator comprising an astable multivibrator including a controlling means comprising a selector connected to a plurality of capacitive reactances that may be selectively and alternatively enabled for varying the charging time between 1.25 and 1.5 microseconds, a comparator having inputs connected to respective outputs of said signal generators, an amplifier circuit having an input connected to an output of the comparator, for amplifying an output signal of the comparator comprised of a high frequency pulse train, a converter circuit connected to an output of the amplifier circuit, for monitoring the amplifier circuit output, and an inductive reactance connected to the output of the amplifier circuit and comprising a means for radiating the pulsing electromagnetic fields, said radiating means being defined by an open circuit coil, wherein one terminal of the coil is connected to the output of said amplifier circuit by means of a coaxial cable, and wherein the inductive reactance of the radiating means is made of flat conductors in a printed circuit.

2. The device of claim 1, wherein the high frequency generator comprises a crystal oscillator.

3. The device of claim 2, including a regulable energy source.

4. The device of claim 2, wherein said flat conductor comprises a flexible flat cable including between 34 to 64 conductors.

5. The device of claim 2, wherein the converter circuit includes a buzzer.

6. A therapeutic apparatus for applying pulsing electromagnetic fields for treating a patient in need of the therapy, the apparatus comprising:

the device of claim 1 and a resting table for receiving the patient, the radiating means comprising at least one radiating strap movably arranged along the table, the strap being selectively located in a proper position for irradiating a desired part of the body of the patient.

7. The apparatus of claim 6, wherein the apparatus comprises a plurality of said straps transversally located in the table, the table also including a fix longitudinal strap in a position to be aligned with the spire of the patient.

8. The apparatus of claim 7, further comprising an irradiating cylinder within a pillow for receiving the head of the patient.

9. A device for applying electromagnetic therapy by sequentially generating pulsing electromagnetic fields for treating a patient in need of the therapy, the apparatus being of the type generating low power electromagnetic pulses, the device comprising:

a high frequency signal generator, a low frequency signal generator comprising an astable multivibrator including a controlling means comprising a selector connected to a plurality of capacitive reactances that may be selectively and alternatively enabled for varying the charging time between 1.25 and 1.5 microseconds, a comparator having inputs connected to respective outputs of said signal generators, an amplifier circuit having an input connected to an output of the comparator, for amplifying an output signal of the comparator comprised of a high frequency pulse train, a converter circuit connected to an output of the amplifier circuit, for monitoring the amplifier circuit output, and an inductive reactance connected to the output of the amplifier circuit and comprising a means for radiating the pulsing electromagnetic fields, said radiating means being defined by an open circuit coil, wherein one terminal of the coil is connected to the output of said amplifier circuit by means of a coaxial cable, and wherein the inductive reactance of the radiating means comprises a flexible flat cable including between 34 to 64 conductors.

10. A therapeutic apparatus for applying electromagnetic therapy by sequentially generating pulsing electromagnetic fields for treating a patient in need of the therapy, the apparatus being of the type generating low power electromagnetic pulses, the apparatus comprising:

a high frequency signal generator, a low frequency signal generator comprising an astable multivibrator including a controlling means comprising a selector connected to a plurality of capacitive reactances that may be selectively and alternatively enabled for varying the charging time between 1.25 and 1.5 microseconds, a comparator having inputs connected to respective outputs of said signal generators, an amplifier circuit having an input connected to an output of the comparator, for amplifying an output signal of the comparator comprised of a high frequency pulse train, a converter circuit connected to an output of the amplifier circuit, for monitoring the amplifier circuit output, an inductive reactance connected to the output of the amplifier circuit and comprising a means for radiating the pulsing electromagnetic fields, said radiating means being defined by an open circuit coil, wherein one terminal of the coil is connected to the output of said amplifier circuit by means of a coaxial cable, and a resting table for receiving the patient, the radiating means comprising at least one radiating strap movably arranged along the table, the strap being selectively located in a proper position for irradiating a desired part of the body of the patient.

11. The apparatus of claim 10, wherein the apparatus comprises a plurality of said straps transversally located in the table, the table also including a fix longitudinal strap in a position to be aligned with the spine of the patient.

12. The apparatus of claim 11, further comprising an irradiating cylinder within a pillow for receiving the head of the patient.

\* \* \* \* \*